US008740944B2

(12) United States Patent
Trieu et al.

(10) Patent No.: US 8,740,944 B2
(45) Date of Patent: Jun. 3, 2014

(54) VERTEBRAL STABILIZER

(75) Inventors: Hai H. Trieu, Cordova, TN (US);
Thomas Carls, Memphis, TN (US);
Jonathan Dewey, Memphis, TN (US)

(73) Assignee: Warsaw orthopedic, Inc., Warsaw, IN (US)

( * ) Notice: Subject to any disclaimer, the term of this patent is extended or adjusted under 35 U.S.C. 154(b) by 1697 days.

(21) Appl. No.: 11/680,401

(22) Filed: Feb. 28, 2007

(65) Prior Publication Data

US 2008/0234736 A1 Sep. 25, 2008

(51) Int. Cl.
*A61B 17/70* (2006.01)

(52) U.S. Cl.
USPC .......................................... 606/254

(58) Field of Classification Search
USPC .......................... 606/86 A, 246–279; 428/188
See application file for complete search history.

(56) References Cited

U.S. PATENT DOCUMENTS

| | | | |
|---|---|---|---|
| 5,217,461 A | 6/1993 | Asher et al. | |
| 5,375,823 A | 12/1994 | Navas | |
| 5,415,661 A | 5/1995 | Holmes | |
| 5,486,174 A | 1/1996 | Fournet-Fayard et al. | |
| 5,591,164 A | 1/1997 | Nazre et al. | |
| 5,593,408 A | 1/1997 | Gayet et al. | |
| 5,609,634 A | 3/1997 | Voydeville | |
| 5,997,542 A | 12/1999 | Burke | |
| 6,093,188 A | 7/2000 | Murray | |
| 6,099,528 A | 8/2000 | Saurat | |
| 6,102,912 A | 8/2000 | Cazin et al. | |
| 6,206,882 B1 | 3/2001 | Cohen | |
| 6,267,764 B1 | 7/2001 | Elberg | |
| 6,379,355 B1 | 4/2002 | Zucherman et al. | |
| 6,652,530 B2 | 11/2003 | Ip et al. | |
| 6,733,531 B1 | 5/2004 | Trieu | |
| 6,966,910 B2 | 11/2005 | Ritland | |
| 6,986,771 B2 | 1/2006 | Paul et al. | |
| 6,989,011 B2 | 1/2006 | Paul et al. | |
| 2003/0171749 A1 | 9/2003 | Le Couedic et al. | |
| 2003/0191470 A1* | 10/2003 | Ritland | ................. 606/61 |
| 2003/0220643 A1 | 11/2003 | Ferree | |
| 2004/0002708 A1 | 1/2004 | Ritland | |
| 2004/0049189 A1 | 3/2004 | Le Couedic et al. | |

(Continued)

FOREIGN PATENT DOCUMENTS

| | | |
|---|---|---|
| EP | 0576379 A1 | 12/1993 |
| EP | 0669109 | 8/1995 |

(Continued)

OTHER PUBLICATIONS

European Patent Office, International Searching Authority,Notification of Transmittal of the International Search Report and the Written Opinion of the International Searching Authority or the Declaration, International Application No. PCT/US2007/065947, Sep. 5, 2007, 2 pages.

(Continued)

*Primary Examiner* — Jan Christopher Merene
*Assistant Examiner* — Steven Cotroneo

(57) ABSTRACT

A bio-compatible stabilization system includes one or more inserters and a connector for traversing a space between one or more bony structures. The stabilization system is designed to reduce or eliminate stress shielding effects while functioning as a tension band. The connector includes an extendable member and an over-extension limiter that limits extension of the extendable member.

34 Claims, 6 Drawing Sheets

(56) References Cited

U.S. PATENT DOCUMENTS

| | | |
|---|---|---|
| 2004/0073215 A1* | 4/2004 | Carli .................................. 606/61 |
| 2004/0102777 A1 | 5/2004 | Huebner |
| 2004/0147928 A1 | 7/2004 | Landry et al. |
| 2004/0215191 A1 | 10/2004 | Kitchen |
| 2004/0236327 A1* | 11/2004 | Paul et al. ......................... 606/61 |
| 2004/0267260 A1 | 12/2004 | Mack et al. |
| 2005/0065515 A1 | 3/2005 | Jahng |
| 2005/0065516 A1 | 3/2005 | Jahng |
| 2005/0085815 A1* | 4/2005 | Harms et al. ..................... 606/61 |
| 2005/0124991 A1 | 6/2005 | Jahng |
| 2005/0143823 A1 | 6/2005 | Boyd et al. |
| 2005/0149020 A1 | 7/2005 | Jahng |
| 2005/0154390 A1 | 7/2005 | Biedermann et al. |
| 2005/0171539 A1 | 8/2005 | Braun et al. |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0203511 A1 | 9/2005 | Wilson-MacDonald et al. |
| 2005/0203513 A1 | 9/2005 | Jahng et al. |
| 2005/0203514 A1* | 9/2005 | Jahng et al. ..................... 606/61 |
| 2005/0203517 A1 | 9/2005 | Jahng et al. |
| 2005/0203518 A1 | 9/2005 | Biedermann et al. |
| 2005/0203519 A1* | 9/2005 | Harms et al. ..................... 606/61 |
| 2005/0209593 A1 | 9/2005 | Kolb |
| 2005/0209694 A1 | 9/2005 | Loeb |
| 2005/0261686 A1 | 11/2005 | Paul |
| 2005/0267471 A1 | 12/2005 | Biedermann et al. |
| 2005/0277922 A1 | 12/2005 | Trieu et al. |
| 2005/0277926 A1 | 12/2005 | Farris |
| 2005/0277932 A1 | 12/2005 | Farris |
| 2006/0009768 A1 | 1/2006 | Ritland |
| 2006/0041259 A1* | 2/2006 | Paul et al. ......................... 606/61 |
| 2006/0064090 A1* | 3/2006 | Park .................................. 606/61 |
| 2006/0079953 A1 | 4/2006 | Gregorich et al. |
| 2006/0084982 A1 | 4/2006 | Kim |
| 2006/0084984 A1 | 4/2006 | Kim |
| 2006/0084987 A1 | 4/2006 | Kim |
| 2006/0095134 A1 | 5/2006 | Trieu et al. |
| 2006/0129147 A1 | 6/2006 | Biedermann et al. |
| 2006/0142758 A1 | 6/2006 | Petit |
| 2006/0142760 A1 | 6/2006 | McDonnell |
| 2006/0155279 A1 | 7/2006 | Ogilvie |
| 2006/0184171 A1* | 8/2006 | Biedermann et al. ........... 606/61 |
| 2006/0229608 A1* | 10/2006 | Foster et al. ..................... 606/61 |

FOREIGN PATENT DOCUMENTS

| | | |
|---|---|---|
| EP | 1388323 A1 | 2/2004 |
| FR | 2 799 949 | 4/2001 |
| GB | 2 382 304 | 5/2003 |
| WO | WO 01/45576 | 6/2001 |

OTHER PUBLICATIONS

U.S. Appl. No. 11/413,448, filed Apr. 28, 2006.
U.S. Appl. No. 11/351,051, filed Feb. 9, 2006.
U.S. Appl. No. 11/563,594, filed Nov. 27, 2007.

* cited by examiner

VERTEBRAL STABILIZER

BACKGROUND

Severe back pain and nerve damage may be caused by injured, degraded, or diseased spinal joints and particularly, spinal discs. Current methods of treating these damaged spinal discs may include vertebral fusion, nucleus replacements, or motion preservation disc prostheses. Disc deterioration and other spinal deterioration may cause spinal stenosis, a narrowing of the spinal canal and/or the intervertebral foramen, that causes pinching of the spinal cord and associated nerves. Current methods of treating spinal stenosis include laminectomy or facet resection. Alternative and potentially less invasive options are needed to provide spinal pain relief.

SUMMARY

In accordance with one aspect of the present disclosure, an implant for stabilizing bony structures is presented. The implant includes a first end, a second end, and an extendable member connected to the first end and the second end. The extendable member is sized to traverse a space between at least two bony structures. The implant further has an over-extension limiter connected to the first end and the second end, and traversing the space between the at least two bony structures. The over-extension limiter is configured to prevent over-extension of the extendable member.

In accordance with another aspect, the present disclosure includes an implant system. The implant system includes a connector having a first and a second extendable member. The first extendable member has a first extendibility and the second member has a second extendibility that is less than the first extendibility. The implant system further includes an inserter designed to engage the connector to position the connector adjacent an anchor securable to a bony structure.

According to another aspect, the present disclosure is directed to a spinal stabilization kit that includes a first bone anchor and a second bone anchor. The kit further includes a connector designed to be anchored to the first bone anchor and the second bone anchor. The connector has a first extendable component and a second extendable component. The second extendable component, when taut, limits farther extension of the first extendable component.

In accordance with yet another aspect of the present disclosure, a system for stabilizing a spinal motion segment is presented. The system includes a first anchor and a second anchor, and a tension member connected to the first anchor and the second anchor and sized to span a distance between at least two vertebral bodies. The tension member is designed to allow limited displacement of the first anchor and the second anchor from one another. The system further includes an extension-limiter member connected to the tension member and sized to span the distance between the at least two vertebral bodies. The extension-limiter member provides an increasing resistance to limited displacement of the first anchor and the second anchor from one another as the extension-limiter member is extended from a relatively relaxed state to a relatively taut state.

According to yet a further aspect, the present disclosure is directed to a surgical method that includes implanting a first bone anchor to a first vertebral body. The surgical method further includes securing one end of a connector to the first bone anchor. The connector has a first tension member and a second, different from the first, tension member designed to limit extension of the first tension member. The method further includes implanting a second bone anchor to a second vertebral body spaced from the first vertebral body and securing another end of the connector to the second bone anchor with tension applied to the first tension member and slack in the second tension member.

These and other aspects, forms, objects, features, and benefits of the present invention will become apparent from the following detailed drawings and descriptions.

DETAILED DESCRIPTION

Figure 1:
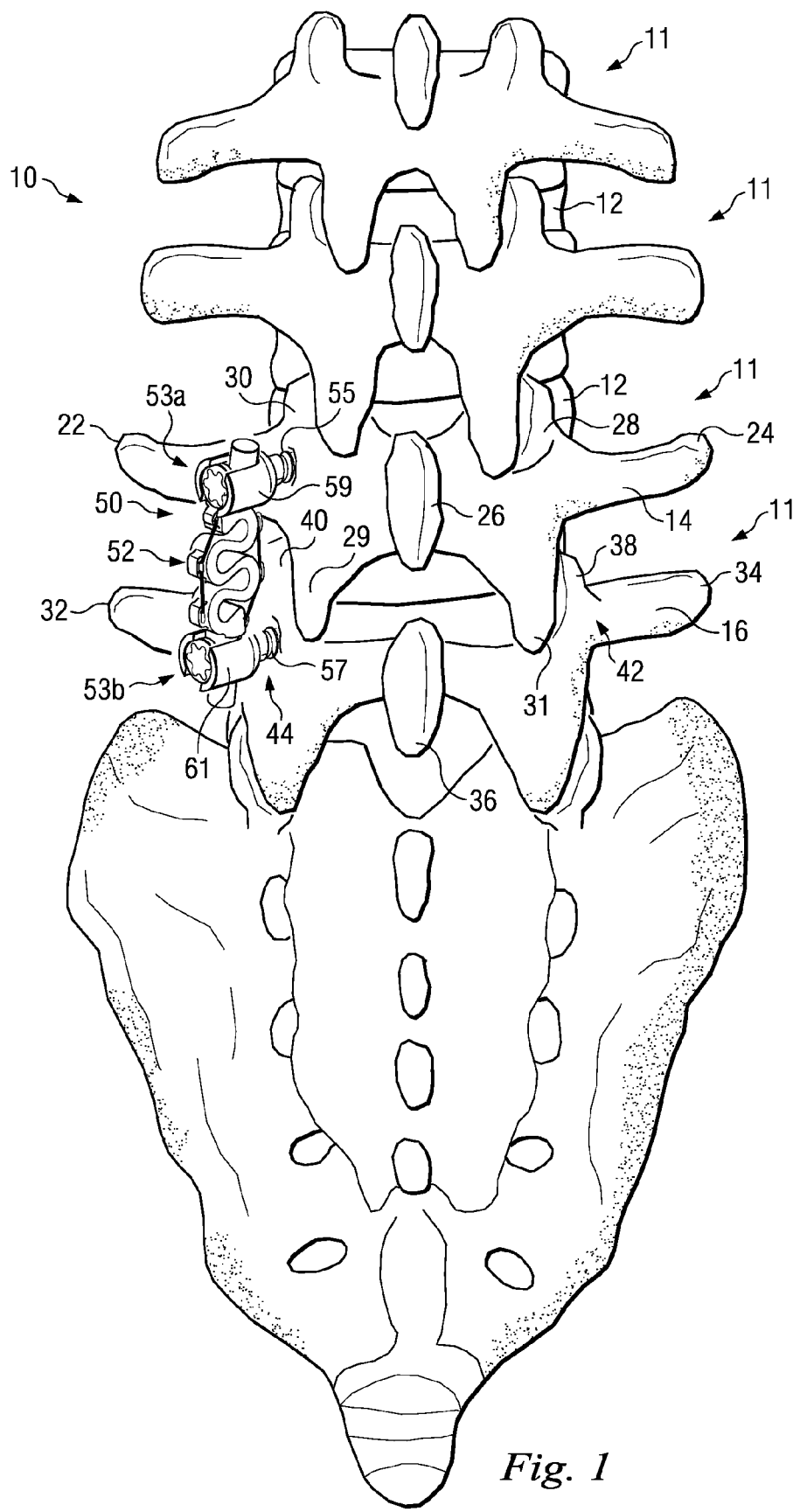
FIG. 1 is a pictorial representation of a vertebral column with a vertebral stabilizing system according to one embodiment of the present disclosure.

The present disclosure relates generally to the field of orthopedic surgery, and more particularly to systems and methods for stabilizing a spinal joint. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring to FIG. 1, the numeral 10 refers to a spinal column having a series of vertebral joints 11, each including an intervertebral disc 12. One of the vertebral joints 11 will be described further with reference to adjacent vertebrae 14, 16. The vertebra 14 includes transverse processes 22, 24; a spinous process 26; superior articular processes 28, 30; and inferior articular processes 29, 31. Similarly, the vertebra 16 includes transverse processes 32, 34; a spinous process 36; superior articular processes 38, 40; and inferior articular processes (not labeled). Although the illustration of FIG. 1 generally depicts the vertebral joint 11 as a lumbar vertebral joint, it is understood that the devices, systems, and methods of this disclosure may also be applied to all regions of the vertebral column, including the cervical and thoracic regions. Furthermore, the devices, systems, and methods of this disclosure may be used in non-spinal orthopedic applications.

A facet joint 42 is formed, in part, by the adjacent articular processes 31, 38. Likewise, another facet joint 44 is formed, in part, by the adjacent articular processes 29, 40. Facet joints also may be referred to as zygapophyseal joints. A healthy facet joint includes a facet capsule extending between the adjacent articular processes. The facet capsule comprises cartilage and synovial fluid to permit the articulating surfaces of the articular processes to remain lubricated and glide over one another. The type of motion permitted by the facet joints is dependent on the region of the vertebral column. For example, in a healthy lumbar region, the facet joints limit rotational motion but permit greater freedom for flexion, extension, and lateral bending motions. By contrast, in a healthy cervical region of the vertebral column, the facet joints permit rotational motion as well as flexion, extension, and lateral bending motions. As the facet joint deteriorates, the facet capsule may become compressed and worn, losing its ability to provide a smooth, lubricated interface between the articular surfaces of the articular processes. This may cause pain and limit motion at the affected joint. Facet joint deterioration may also cause inflammation and enlargement of the facet joint which may, in turn, contribute to spinal stenosis. Removal of an afflicted articular process may result in abnormal motions and loading on the remaining components of the joint. The embodiments described below may be used to stabilize a deteriorated facet joint while still allowing some level of natural motion.

Injury, disease, and deterioration of the intervertebral disc 12 may also cause pain and limit motion. In a healthy intervertebral joint, the intervertebral disc permits rotation, lateral bending, flexion, and extension motions. As the intervertebral joint deteriorates, the intervertebral disc may become compressed, displaced, or herniated, resulting in excess pressure in other areas of the spine, particularly the posterior bony elements of the afflicted vertebrae. This deterioration may lead to spinal stenosis. In one application, the embodiments described below may restore more natural spacing to the posterior bony elements of the vertebrae, decompress an intervertebral disc, and/or may relieve spinal stenosis. Referring still to FIG. 1, in one embodiment, a vertebral stabilizing system 50 may be used to provide support to the vertebrae 14, 16, at least partially decompress the disc 12 and the facet joint 44, and/or relieve stenosis.

Connected at each end to vertebral fasteners 53(a), 53(b), a flexible connector 52, such as a spring rod, may provide compressive support and load distribution, and thereby providing relief to the intervertebral disc 12. In addition, the flexible connector 52 may dampen the forces on the intervertebral disc 12 and facet joint 44 during motion such as flexion. Because the flexible connector 52 is securely connected to the vertebral fasteners 53(a), 53(b), the flexible connector 52 also provides relief in tension. Accordingly, during bending or in extension, the flexible connector 52 may assist in providing a flexible dampening force to limit the chance of overcompression or overextension when muscles are weak. In addition, the flexible connector 52 allows at least some torsional movement of the vertebra 14 relative to the vertebra 16. In one exemplary embodiment, the fasteners 53(a), 53(b) include a pedicle screw 55, 57 that together with anchors 59, 61 secure the flexible connector 52 in place. Such an exemplary fastener is described in U.S. Patent App. Pub. No. 2005/0277922, the disclosure of which is incorporated herein by reference.

Figure 2:
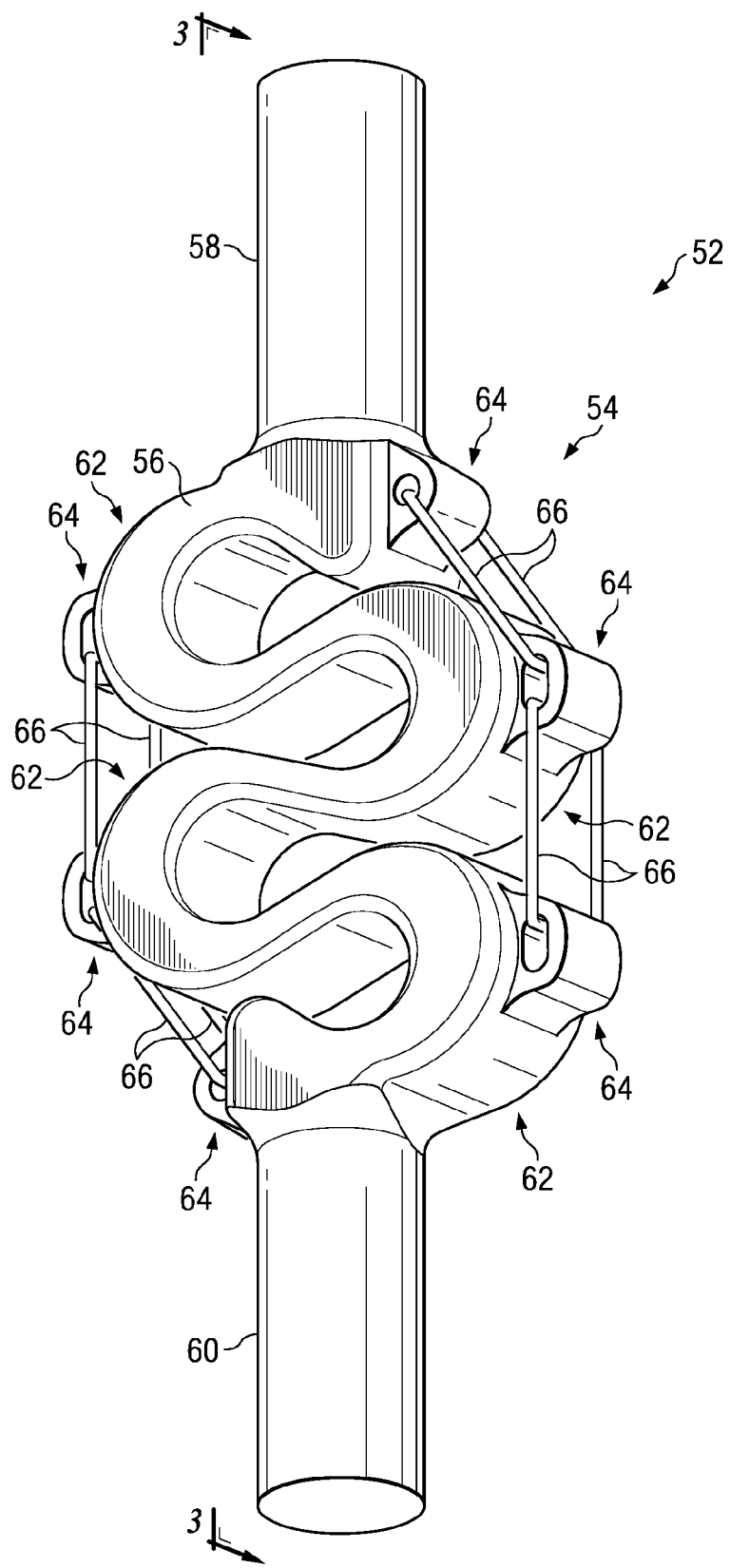
FIG. 2 is a perspective view of a connector in a relatively relaxed condition according to one embodiment of the present disclosure.

FIG. 2 shows an exemplary embodiment of the flexible connector 52 in greater detail. In this embodiment, the flexible connector 52 is shown as including a spring rod; however, it is understood that the other types of rods may be used.

Connector 52 includes a spring rod 54 having an anteriorly located center of rotation. The spring rod 54 includes a relatively elastic serpentine body 56 centrally positioned between ends 58, 60. In the illustrative embodiment, the ends 58, 60 are generally cylindrical, but it is recognized that the ends may have other profiles, such as, polygonal, oval, and flat, for example. As shown in FIG. 2, the serpentine body 56 defines a series of curved portions 62 that support compression and extension of the spring rod 54 when appropriately loaded. That is, when the spring rod 54 is placed under tension from spinal extension, for example, ends 58, 60 are pulled away from one another by movement of the spine. As a result, the elasticity of the serpentine body 56 allows for elongation of the spring rod 54 to provide spinal support during spinal extension.

Conventional spring rods, and other connectors, can be susceptible to early fatigue generally associated with over-extension of the connector during spinal extension, flexion, and rotation. In this regard, the present disclosure includes a connector with an over-extension limiter. In one example, the connector is constructed to include relatively inelastic components that effectively provide extension stops on the relatively elastic connector or spring rod. It is understood that "elastic" and "inelastic" are relative terms and the materials used for the inelastic components may have an elasticity albeit reduced relative to the elasticity of the elastic components. It is also contemplated that the a desired elasticity response for the connector 52 may be achieved by utilizing various types of elastic and inelastic materials in a single implementation. That is, the invention is not limited to a connector having a single-type of elastic components and a single type of inelastic components.

Referring again to FIG. 2, the spring rod body 54 is constructed to have a series of anchors 64 that are threaded with a relatively inelastic member 66, such as a band, tether, cord, wire, and the like. In the embodiment illustrated in FIG. 2, the anchors 64 are formed on outer wall of the curved portions 62 of the spring rod body 54. In one embodiment, the anchors 64 are integral with the spring rod body 62 and are formed during formation of the spring rod body; however, it is contemplated that the anchors may be joined or otherwise coupled to the spring rod body using adhesive or other suitable means. In the illustrated example, the serpentine body 62 has six anchors 64 and four inelastic members 66 with each curved portion having an anchor, but it is recognized that fewer or more inelastic members could be used and that inelastic members may extend beyond an adjacent curved portion.

Figure 3:
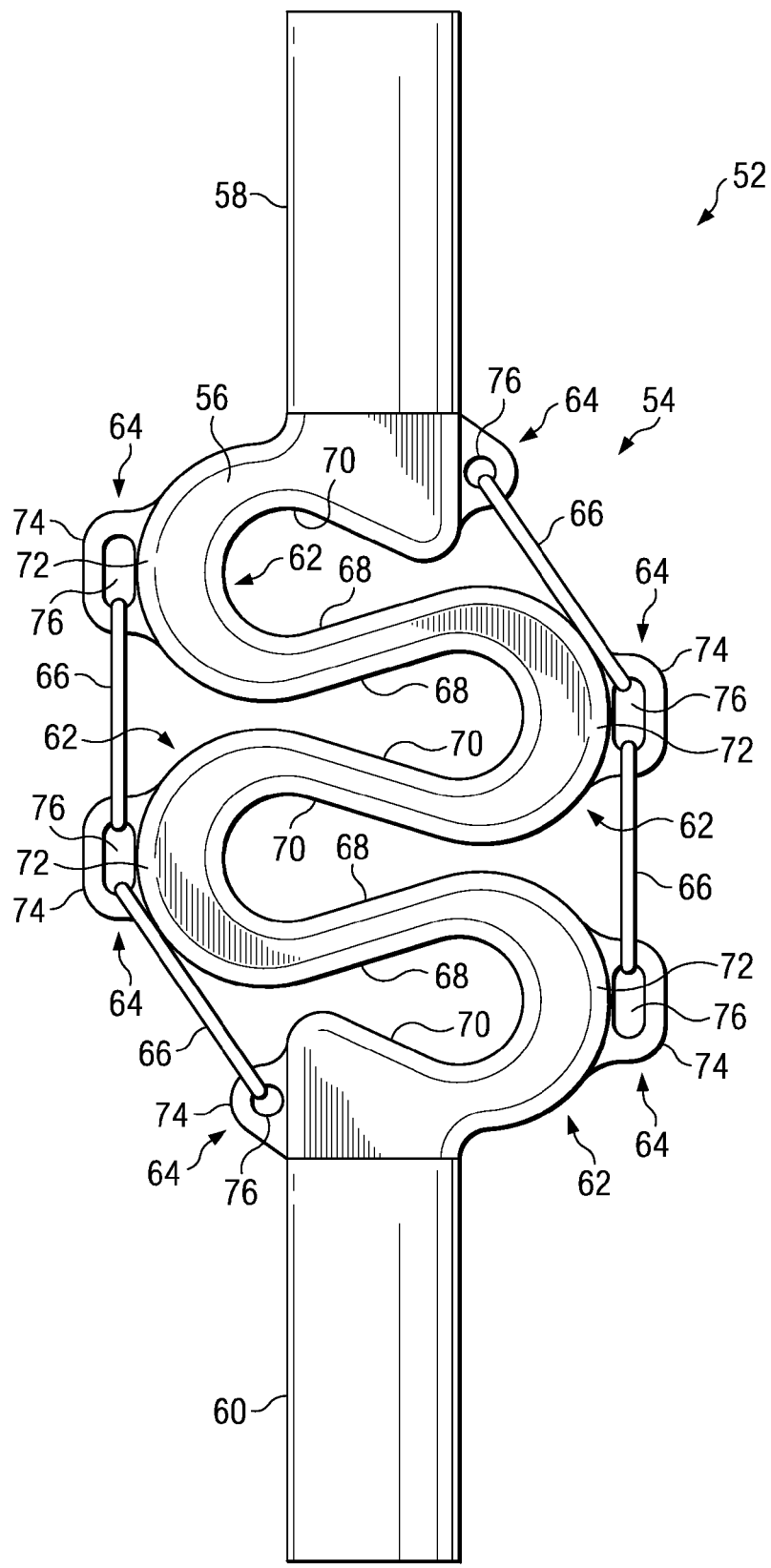
FIG. 3 is a side elevation view of the connector of FIG. 2.

Referring now to FIG. 3, a side elevation view of the connector illustrated in FIG. 2 is shown. The inelastic members 66 traverse a single curved portion 62. That is, each curved portion 62 is defined by a pair of legs 68, 70 that are connected to one another by a curved face 72. In the illustrated example, each anchor 64 includes an anchor body 74 extending from face 72. The anchor body 74 further has an opening 76 extending therethrough for passage of an inelastic member. As noted above, the anchor bodies 74 may be integrally formed with or otherwise affixed to faces 72.

The inelastic members 66, which may take the form of tethers, bands, cords, wire, and the like, are looped between adjacent anchors. Thus, in the illustrated example, the centrally located anchors each have two inelastic members whereas the outer anchors have only a single inelastic member. The inelastic members are designed to support the spring rod when the spring rod is under tension. As such, the inelastic members have a slight extendibility to support extension of the spring rod body, but as the spring rod body is extended, the extendibility of the inelastic members is consumed and the inelasticity prevents further extension. In this regard, the inelastic members are preferably installed in a relaxed state and when taut, prevent over-extension of the spring rod body.

The extendibility of the inelastic members can be defined by their composition, installation with slack, or both. It is contemplated that the inelastic members may have a fibered construction such that the fibers are arranged to provide a certain degree of elasticity. That is, the inelastic members can be constructed such that the fibers are unaligned when in a relaxed state and thus will allow uninhibited extension of the spring rod body until the fibers begin to align with one another. As the fibers begin to align with another, the inelastic member begins to fight further extension of the spring rod body. As the spring rod body is extended by virtue of spinal extension, flexion, or rotation, the inelastic members provide an increasing resistance to such extension. In one example, the inelasticity of the inelastic members is such that full extension of the spring body is prevented.

In another example, the inelastic members are installed with slack. As such, the inelastic members are installed such that the length of the inelastic members is greater than the distance between adjacent anchors when the spring rod body is in a relaxed state. Thus, as the spring rod body is extended, the distance between anchors increases which results in the slack in the inelastic members being consumed. When the slack is fully consumed, the inelasticity of the inelastic members resists further extension of the spring rod body, i.e., further displacement of the anchors from one another. Accordingly, the amount of slack present in the inelastic member defines the distance the spring rod body will be allowed to extend before the bias of the inelastic members is placed on the spring rod body. Furthermore, unlike the embodiment described in the preceding paragraph, the resistance does not increase as the spring rod body is extended. In other words, the inelastic members do not place a resistance on extension of the spring rod body until the slack is consumed.

It is also contemplated that the inelastic members can be designed to have a fibered or similar construction that resists extension of the spring rod body as the fibers become more aligned, but be installed so that a slack is present between adjacent anchors. In this embodiment, the spring rod body is permitted to extend as the slack of the inelastic members is consumed. Once that slack is consumed, the inelastic members begin to resist further extension of the spring rod body. That resistance increases as the spring rod is further extended until the fibers in the inelastic members are aligned and the bias of inelastic members is greater than the load imposed by the spinal movement, at which the spring rod body is prevented from further extension.

Figure 4:
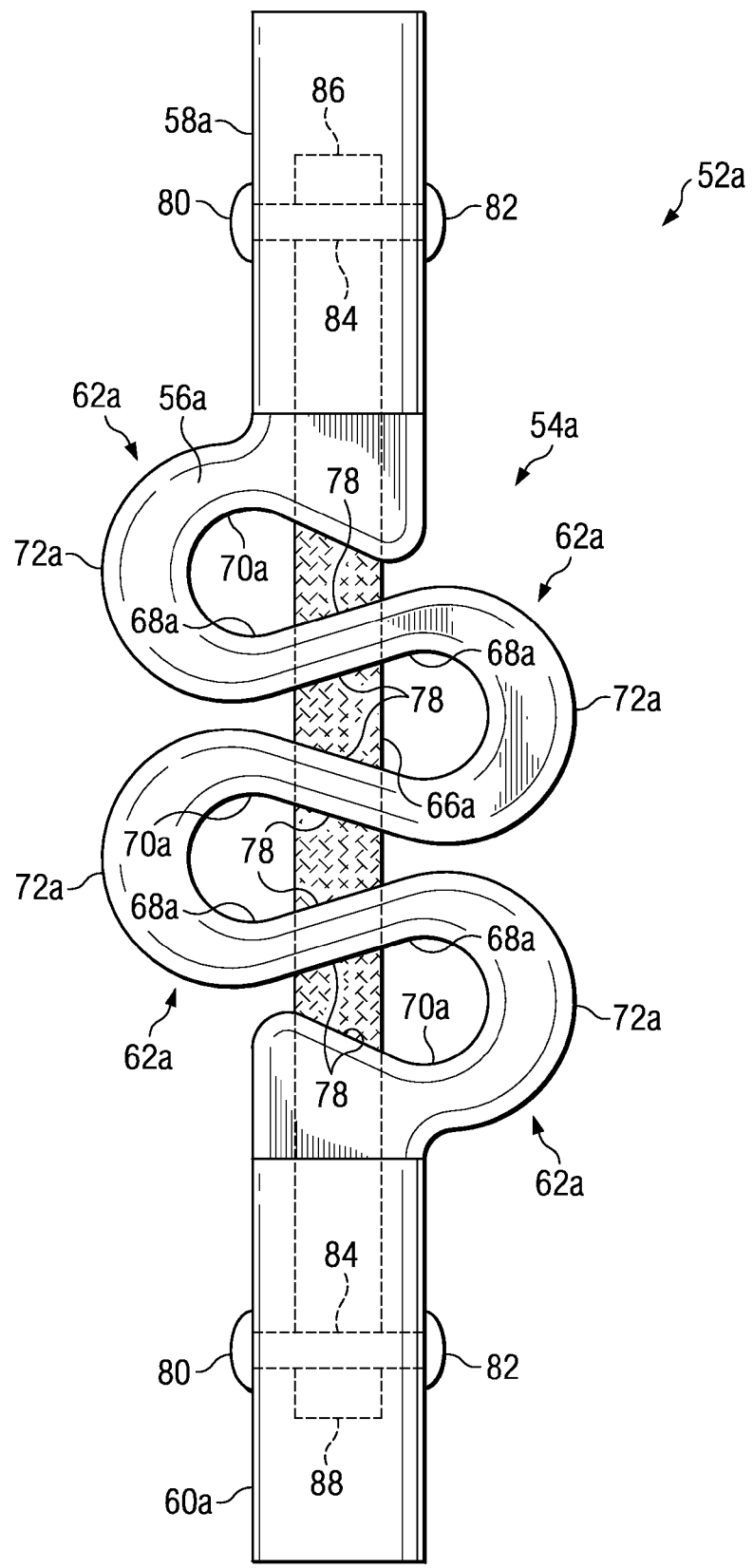
FIG. 4 is a side elevation view of a connector according to another embodiment of the present disclosure.
Figure 5:
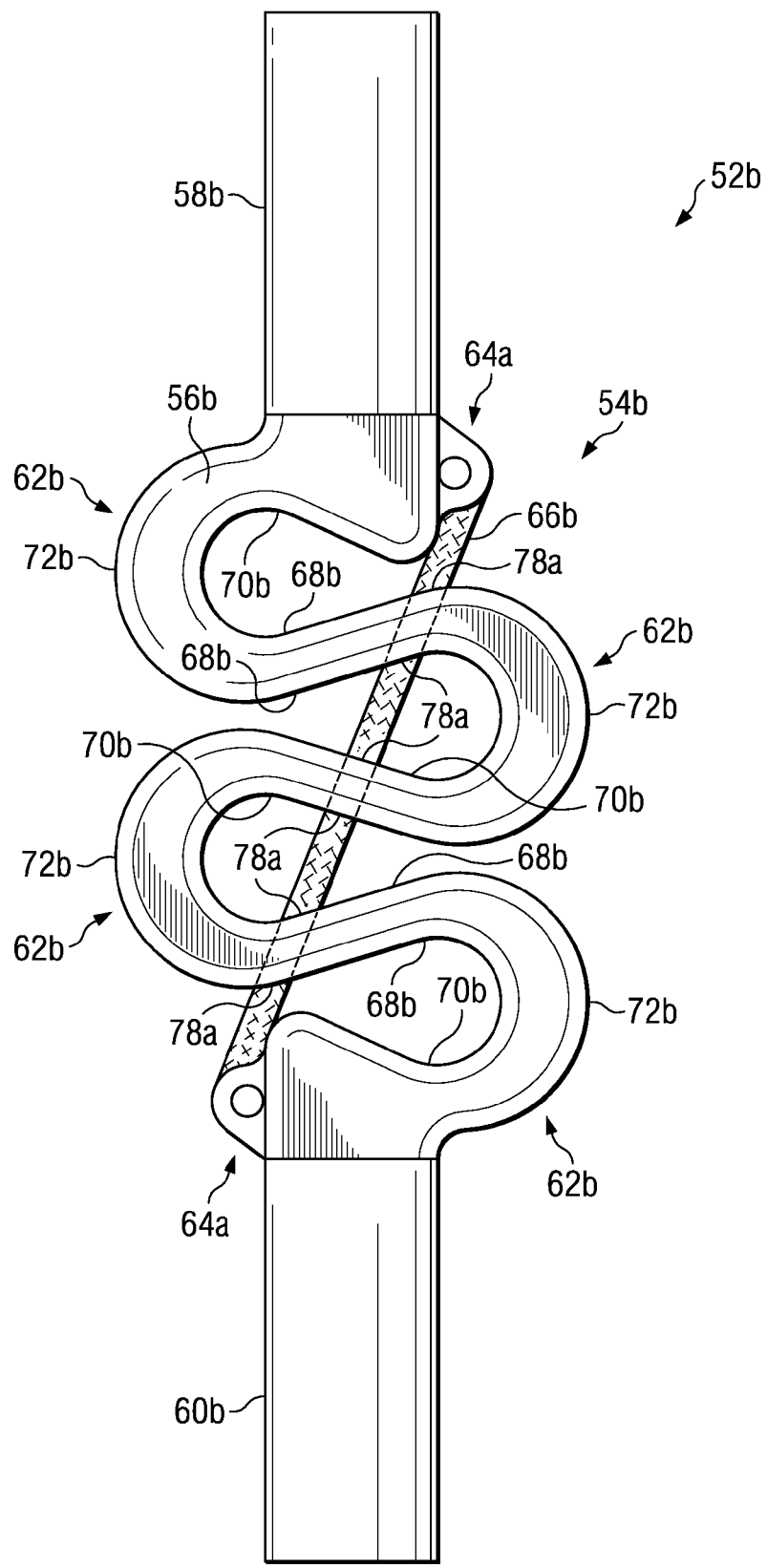
FIG. 5 is a side elevation view of a connector according to yet another embodiment of the present disclosure.
Figure 6:
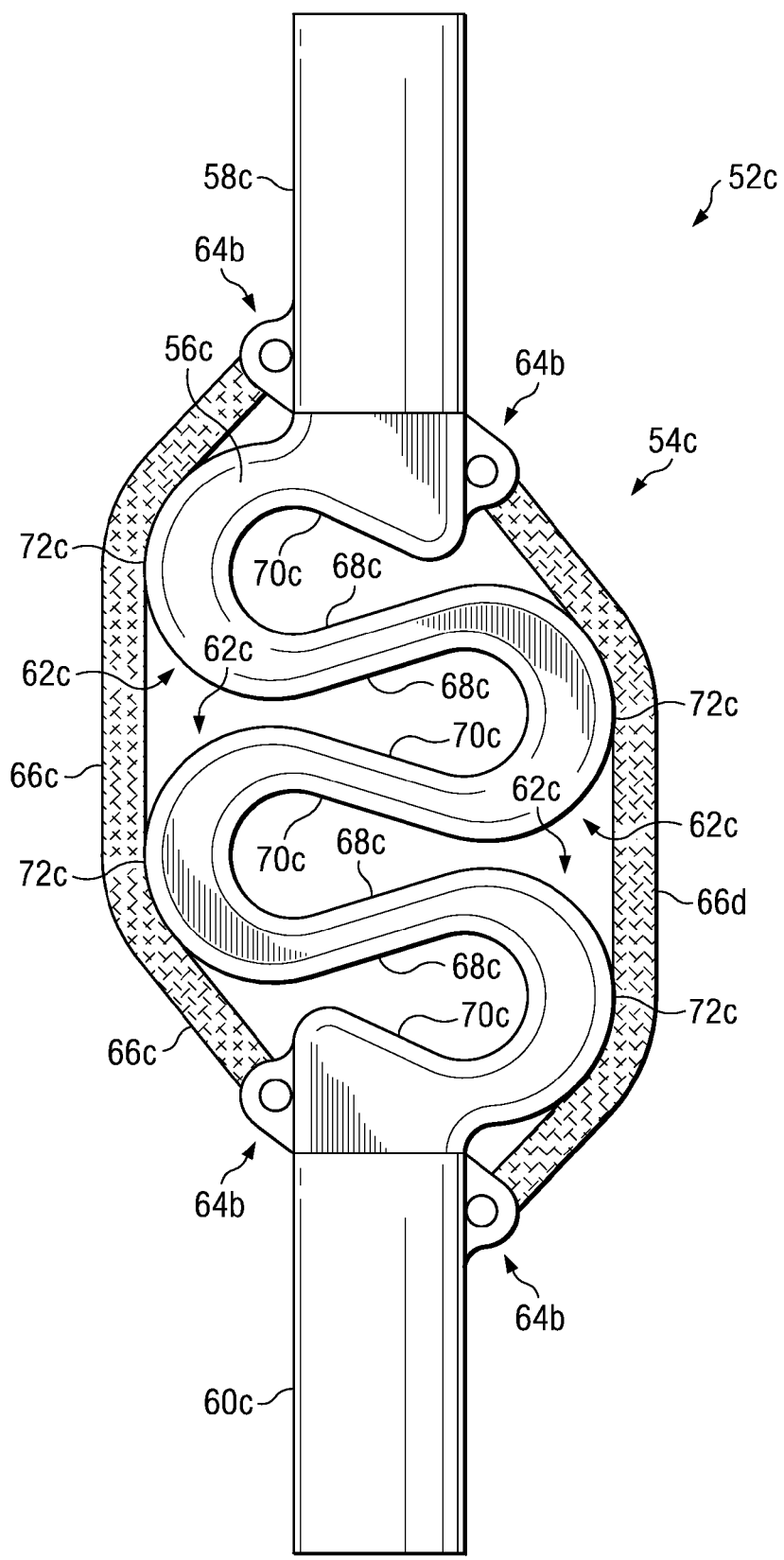
FIG. 6 is a side elevation view of a connector according to a further embodiment of the present disclosure.

FIGS. 4-6 show connectors according to additional embodiments of the present disclosure. The illustrated embodiments are examples of connectors constructed according to the present disclosure; however, the present disclosure is not limited to the illustrated connectors.

FIG. 4 shows a connector $52(a)$ wherein openings 78 are formed in the legs $68(a)$, $70(a)$ of the curved portions $62(a)$. The openings 78 are linearly aligned with another and in-line with ends $58(a)$, $60(a)$. An inelastic member $66(a)$ extends through the openings 78 and into ends $58(a)$, $60(a)$. In the illustrated example, a locking screw 80 and nut 82 are used to fasten the inelastic member $66(a)$ to the spring rod $54(a)$. In one example, bores 84 are defined at each end 86, 88 of the inelastic member $66(a)$ that receive the shaft of locking pin 80. It is recognized that other attachment devices and techniques may be used to couple the inelastic member to the spring rod. For example, the inelastic member may be adhesively secured to the cylindrical ends. Construction and operation of the inelastic member $66(a)$ is similar to that described above; however, in this example, only a single inelastic member is shown. But, it is contemplated that multiple inelastic members may be used and those multiple inelastic members may extend through a common set of openings or have respective sets of openings formed in the serpentine body $56(a)$.

FIG. 5 illustrates another connector $52(b)$ according to another embodiment of the present disclosure. In this embodiment, a series of openings $78(a)$ are formed in the serpentine body and are aligned with one another to define a diagonal channel through the serpentine body. An inelastic member $66(b)$ is disposed through the diagonal channel and is secured to the serpentine body by anchors $64(a)$. As the openings through the serpentine body form a diagonal channel, the anchors are on opposing surfaces of the spring rod $54(b)$.

FIG. 6 illustrates yet another connector according to another embodiment of the present disclosure. Similar to the connector shown in FIGS. 2-3, the connector $52(c)$ has multiple inelastic members $66(c)$, $66(d)$ extending along a periphery of the serpentine body $56(c)$ of the spring rod $54(c)$. However, the anchors $64(b)$ are formed on the cylindrical ends $58(c)$, $60(c)$ rather than the curved portions $62(c)$ of the serpentine body $56(c)$. With this construction, as the spring rod $54(c)$ is extended, the serpentine body $56(c)$ lengthens and the height of the curved portions $62(c)$ decreases. As the spring rod $54(c)$ is stretched, the anchors $64(b)$ are moved farther away from one another which causes slack in the inelastic members $66(c)$, $66(d)$ to be consumed. That is, when the spring rod $54(c)$ is at rest, the curved portions $62(c)$ of the serpentine body $56(c)$ are formed to have a height that extends into a path defined along the shortest distance between the anchors $64(b)$. Thus, to connect to the anchors $64(b)$, the length of inelastic members $66(c)$, $66(d)$ is greater than the distance between the anchors $64(b)$. This creates some slack in the inelastic members $66(c)$, $66(d)$. As the height of the curved portions $62(c)$ is decreased as a result of extension of the spring rod $54(c)$, the slack is consumed. Accordingly, the inelastic members $66(c)$, $66(d)$ do not resist extension of the spring rod $54(c)$ until the slack is consumed.

In one embodiment, the connector $52(c)$ includes a valley or channel (not shown) formed in the sidewalls of the of the serpentine body $56(c)$. The channels provide a track in which the inelastic members $66(c)$, $66(d)$ fit, and thus slide as the serpentine body is extended and contracted. In this regard, the inelastic members $66(c)$, $66(d)$ are prevented from sliding off the serpentine body. Alternately, eyelets or other similar structures (not shown) could be formed with or otherwise attached to the serpentine body to provide a closed track in which the inelastic members $66(c)$, $66(d)$ can be retained.

The Channels

The flexible connectors 52 described herein may be placed directly adjacent the vertebrae 14, 16, or alternatively, may be spaced from the vertebrae 14, 16. In some embodiments, placement of the flexible connector 52 directly adjacent the vertebrae 14, 16 may impart specific characteristics to the flexible connector 52. In some examples, the flexible connector 52 may be spaced from the vertebrae 14, 16. Accordingly even when the vertebral column is in flexion, causing the spine to bend forward, the first and second vertebral fasteners 54, 56 maintain a line of sight position, so that the flexible connector 52 extends only along a single axis, without bending. In other examples, after placement, the flexible connector 52 may contact portions of the vertebrae 14, 16 during the flexion process. For example, during flexion, the vertebrae 14, 16 may move so that the first and second vertebral fasteners 54, 56 do not have a line of sight position. Accordingly, the flexible connector 52 may be forced to bend around a protruding portion of the vertebrae. This may impart additional characteristics to the flexible connector 52. For example, because the flexible connector 52 would effectively contact the spinal column at three locations (its two ends 58, 60 and somewhere between the two ends), its resistance to extension might be increased.

In the exemplary embodiments described, the flexible connector 52 is the only component extending from one vertebral fastener 54, 56 to the other. This may be referred to as a single flexible connector. This single flexible connector may be contrasted with conventional systems that employ more than one connector extending between attachment points, such as systems with one component connected at the attachment points and another component extending between attachment points. Because it employs a single flexible connector 52, the vertebral stabilizing system 50 disclosed herein may be easier and quicker to install, may be less complex, and may be more reliable than prior devices.

It should be noted however, that a spinal column may employ the flexible connector 50 to extend across a first vertebral space, with a second flexible connector extending across a second vertebral space. Accordingly, more than one vertebral stabilizing system 50 may be used in a spinal column. In some instances where more than one stabilizing system is use, the first and second vertebral spaces may be adjacent. In alternative embodiments, a vertebral stabilizing system 50 may have a single flexible connector with a length allowing it to extend across more than one intervertebral space, with or without connecting to an intermediate vertebra.

In certain anatomies, the vertebral stabilizing system 50 may be used alone to provide decompression or compression to a single targeted facet joint or to relieve pressure on a particular side of the intervertebral disc, such as a herniation area. However, in some instances, a second vertebral stabilizing system may be installed on the opposite lateral side of the vertebrae 14, 16, across from the vertebral stabilizing system 50. Use of first and second vertebral stabilizing systems may provide more balanced support and equalized stabilization. The second vertebral stabilizing system may be substantially similar to system 50 and therefore will not be described in detail.

The vertebral stabilizing system 50, as installed, may flexibly restrict over-compression of the vertebrae 14, 16, thereby relieving pressure on the intervertebral disc 12 and the facet joint 44. In addition, the vertebral stabilizing system 50 may flexibly restrict axial over-extension of the intervertebral disc 12 and the facet joint 44. By controlling both compression and extension, the vertebral stabilizing system 50 may reduce wear and further degeneration. The flexible connector 52 may also dampen the forces on the intervertebral disc 12 and facet joint 44 during motion such as flexion and extension. Because the flexible connector 52 may be positioned relatively close to the natural axis of flexion, the vertebral stabilizing system 50 may be less likely to induce kyphosis as compared to systems that rely upon inter-spinous process devices to provide compressive and tensile support. Additionally, the system 50 may be installed minimally invasively with less dissection than the inter-spinous process devices of the prior art. Furthermore, an inter-pedicular system can be used on each lateral side of the vertebrae 14, 16, and may provide greater and more balanced stabilization than single inter-spinous process devices.

It should be noted that in some embodiments, the flexible connector 52 may be configured so that orientation in one direction provides one set of stabilizing properties to the vertebrae, while orienting the flexible connector 52 in the other direction would provide a second set of stabilizing properties.

As described above, the flexible connector 52 can be made of elastic or semi-elastic materials in parts or in its entirety. Moreover, the serpentine body 56 may likewise be made of elastic or semi-elastic materials, and further include inelastic components. Exemplary elastic materials include polyurethane, silicone, silicone-polyurethane, polyolefin rubbers, hydrogels, and the like. The elastic materials can be resorbable, semi-resorbable, or non-resorbable. Exemplary inelastic materials include polymers, such as polyetheretherketone (PEEK), polyetherketoneketone (PEKK), and polylactic acid materials (PLA and PLDLA), metals, such as titanium, NITINOL, and stainless steel, and/or ceramics, such as calcium phosphate and alumina. Further, the various connector components can be solid, hollow, semi-hollow, braided, woven, mesh, porous, or combinations thereof. The connector can also be reinforced or semi-reinforced.

Although disclosed as being used at the posterior areas of the spine, the flexible connector may also be used in the anterior region of the spine to support the anterior column. In such a use, the flexible connector may be oriented adjacent to and connect to the anterior column, and may span a vertebral disc space.

The foregoing embodiments of the stabilization system may be provided individually or in a kit providing a variety of sizes of components as well as a variety of strengths for the connector. It is also contemplated that the connector's characteristics may be color coded or otherwise indicated on the connector itself to expedite identification of a desired connector.

The invention is also embodied in a surgical method for spinal or other bone stabilization. In accordance with this method, a surgeon performs a conventional interbody fusion/nucleus replacement/disc replacement followed by placement of pedicles/bone screws or other inserters into appropriate vertebral or other bony structures. The surgeon may then anchor one end of a connector into a first vertebral or other bony structure. If necessary or otherwise desired, tension is applied to the connector spanning the space between bony structures. Preferably, tension is applied in a limited manner so that inelastic components of the connector are imposing little or no resistance on the applied tension. The un-anchored end of the connector is then anchored to a second vertebral or other bony structure spaced from the first vertebral or other bony structure. Any excess connector extending past the inserters is preferably cut and removed.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. Further, the embodiments of the present disclosure may be adapted to work singly or in combination over multiple spinal levels and vertebral motion segments. Also, though the embodiments have been described with respect to the spine and, more particularly, to vertebral motion segments, the present disclosure has similar application to other motion segments and parts of the body. In the claims, means-plus-function clauses are intended to cover the elements described herein as performing the recited function and not only structural equivalents, but also equivalent elements.

We claim:

1. An implant for stabilizing bony structures, the implant comprising:

a body extending along a longitudinal axis between a first end and a second end;

a serpentine extendable member having a first portion connected to the first end and an opposite second portion connected to the second end, the first and second portions extending parallel to the longitudinal axis, the extendable member traversing a space between at least two bony structures, at least one of the first and second portions including a first opening, the extendable member having a curved portion that is offset from the longitudinal axis, the curved portion including a second opening; and an over-extension limiter connected through the first and second openings, the over-extension limiter configured to prevent over-extension of the extendable member, wherein the over-extension limiter extends through the first opening of the first portion, the extendable member includes a second curved portion that is spaced apart from the curved portion, the second curved portion including a third opening, and the implant comprises a second over-extension limiter connected through the first opening of the second portion and the third opening.

2. The implant of claim 1 wherein the over-extension limiter comprises inelastic material.

3. The implant of claim 2 wherein the over-extension limiter comprises slack when in a relaxed state and the slack is consumed during extension of the extendable member and wherein the over-extension limiter prevents further extension of the extendable member when the slack is fully consumed.

4. The implant of claim 3 wherein the extendable member has a first length and the over-extension limiter has a second length that is less than the first length.

5. The implant of claim 1 wherein the extendable member includes a third curved portion positioned between the second portion and the second curved portion, the third curved portion including a fourth opening, and the implant comprises a third over-extension limiter connected through the second opening and the fourth opening.

6. The implant of claim 5 wherein the extendable member includes a fourth curved portion positioned between the first portion and the first curved portion, the fourth curved portion including a fifth opening, and the implant comprises a fourth over-extension limiter connected through the third opening and the fifth opening.

7. The implant of claim 6 wherein the first and second over-extension limiters extend transverse to the longitudinal axis and the third and fourth over-extension limiters extend parallel to the longitudinal axis.

8. The implant of claim 7 wherein the second over-extension limiter is spaced from the fourth over-extension limiter.

9. The implant of claim 56 wherein the first over-extension limiter is spaced apart from the third over-extension limiter.

10. The implant of claim 1 wherein the over-extension limiter engages an outer surface of the curved portion.

11. The implant of claim 1 wherein the over-extension limiter is configured to limit extension of the extendable member to a distance of 5 mm.

12. The implant of claim 1 configured to operate according to a non-linear stress-strain elasticity curve.

13. The implant of claim 1 wherein the extendable member and the over-extension limiter are formed of bio-compatible material(s).

14. The implant of claim 1 further comprising a plurality of anchors, a respective anchor disposed at each of the first portion, the second portion and the curved portion, the first opening(s) and the second opening each extending through one of the anchors.

15. The implant of claim 1 wherein the bony structures are vertebral bodies.

16. An implant system comprising:

a connector extending along a longitudinal axis between a first end and a second end, the connector having a first extendable member and a second extendable member, the first extendable member being integrally formed with the second extendable member, the first extendable member including a first portion extending parallel to the axis including a first opening, the second extendable member including a second portion extending parallel to the axis including a second opening, the first extendable member and the second extendable member being S-shaped; and an over-extension limiter connected through the first and second openings, wherein the first and second openings are aligned on a first side of the connector, the first portion includes a third opening positioned on a second side of the connector opposite the first side, the second portion includes a fourth opening positioned on the second side of the connector, the third and fourth openings being aligned on the second side of the connector, and a second over-extension limiter is connected through the third and fourth openings.

17. The implant system of claim 16 wherein the over-extension limiter has a length that is greater than that of the connector.

18. The implant system of claim 17 wherein the over-extension limiter is formed of inelastic material(s).

19. The implant system of claim 18 wherein the connector includes first, second, third and fourth curved portions, an inner surface of the connector defining a third opening positioned between the first and second curved portions, a fourth opening positioned between the second and third curved portions and a fifth opening positioned between the third and fourth curved portions, the over-extension limiter spanning transverse to the longitudinal axis through the first, second, third, fourth and fifth openings.

20. The implant system of claim 16 wherein the over-extension limiter has slack when in a relaxed state and is configured such that the slack is consumed as the connector is extended relative to the body.

21. The implant system of claim 16 wherein the connector has a length sufficient to span a space between adjacent bony structures or between non-adjacent bony structures.

22. A spinal stabilization kit comprising:

a first bone anchor;

a second bone anchor; and a connector extending along a longitudinal axis, the connector being designed to be anchored to the first bone anchor and the second bone anchor, the connector having a first extendable component including a first portion extending parallel to the axis including a first opening and a second extendable component including a second portion extending parallel to the axis including a second opening, the first extendable component being integrally formed with the second extendable component, the first extendable component including a serpentine configuration and having a first curved portion including a third opening and the second extendable component having a serpentine configuration and comprising a second curved portion including a fourth opening an over-extension limiter is connected through the first and third openings or the second and fourth openings and, when taut, limits farther extension of at least one of the first extendable component and the second extendable component relative to at least one of the first and second bone anchors, wherein the over-extension limiter comprises a first over-extension limiter and a second over-extension limiter, the first over-extension limiter being connected through the first and third openings and the second over-extension limiter being connected through the second and fourth openings.

23. The kit of claim 22 wherein the over-extension limiter comprises inelastic material.

24. The kit of claim 22 wherein the first extendable component includes a third curved portion that is spaced apart from the first curved portion, the third curved portion including a fifth opening, and a third over-extension limiter is connected through the fourth and fifth openings.

25. The kit of claim 22 wherein the connector is configured to allow limited displacement of the first anchor from the second anchor when engaged thereto.

26. A system for stabilizing a spinal motion segment, the system comprising:
a first anchor and a second anchor;
a serpentine tension member extending along a longitudinal axis between a first end and a second end, the first end including an inner surface defining a first passageway, the second end including an inner surface defining a second passageway, the tension member being connected to the first anchor and the second anchor and sized to span a distance between at least two vertebral bodies, the tension member having first, second, third and fourth curved faces, the tension member having a first opening positioned between the first and second curved faces, a second opening positioned between the second and third curved faces and a third opening positioned between the third and fourth curved faces, the first, second and third openings being coaxial with the longitudinal axis and wherein the first, second and third openings extend through surfaces of the tension member that extend transverse to the longitudinal axis, the tension member designed to allow limited displacement of the first anchor and the second anchor from one another; and
an extension-limiter member connected through the first and second passageways and the first, second and third openings, the extension-limiter member providing an increasing resistance to limited displacement of the first anchor and the second anchor from one another as the extension-limiter member is extended from a relatively relaxed state to a relatively taut state.

27. The system of claim 26 wherein the first end includes a first aperture and the second end includes a second aperture, the first and second apertures each extending perpendicular to the longitudinal axis, the first and second apertures each having a pin disposed therein that extends through the extension-limiter member to fix the extension-limiter member relative to the first and second ends.

28. The system of claim 26 wherein the extension-limiter member is braided.

29. The system of claim 26 wherein the extension-limiter member is formed of inelastic material(s).

30. The system of claim 26 wherein the extension-limiter member has a length greater than that of the tension member.

31. A surgical method comprising the steps of:
implanting a first bone anchor to a first vertebral body;
securing one end of a connector to the first bone anchor, the connector having a first portion extending parallel to the axis including a first opening, the connector having a curved portion that is offset from the axis including a second opening, the connector including an over-extension limiter extending through the first and second openings designed to limit extension of the connector relative to the first bone anchor, wherein the over-extension limiter extends through the first opening of the first portion, the connector includes a second curved portion that is spaced apart from the curved portion, the second curved portion including a third opening, and the implant comprises a second over-extension limiter connected through the first opening of the second portion and the third opening;
implanting a second bone anchor to a second vertebral body spaced from the first vertebral body; and
securing another end of the connector to the second bone anchor with tension applied to the first tension member and slack in the second tension member.

32. The surgical method of claim 31 further comprising the step of extending the connector before securing the another end to apply tension thereto.

33. The surgical method of claim 32 wherein the step of extending is carried out such that the connector spans a distance between two adjacent vertebral bodies.

34. The surgical method of claim 32 wherein the step of extending is carried out such that the connector spans a distance between two non-adjacent vertebral bodies.

* * * * *